(12) United States Patent
Altmann

(10) Patent No.: US 6,739,721 B2
(45) Date of Patent: May 25, 2004

(54) METHOD AND APPARATUS FOR CALIBRATING AND CERTIFYING ACCURACY OF A WAVEFRONT SENSING DEVICE

(75) Inventor: Griffith E. Altmann, Webster, NY (US)

(73) Assignee: Bausch and Lomb, Inc, Rochester, NY (US)

( * ) Notice: Subject to any disclaimer, the term of this patent is extended or adjusted under 35 U.S.C. 154(b) by 134 days.

(21) Appl. No.: 10/013,573

(22) Filed: Dec. 11, 2001

(65) Prior Publication Data

US 2003/0112410 A1 Jun. 19, 2003

(51) Int. Cl.⁷ ................................................ A61B 3/10
(52) U.S. Cl. ......................................... 351/212; 351/200
(58) Field of Search ................................ 351/200, 211, 351/212; 356/511, 515, 128

(56) References Cited

U.S. PATENT DOCUMENTS

| | | | |
|---|---|---|---|
| 5,066,120 A | 11/1991 | Bertrand | 356/124 |
| 5,151,752 A * | 9/1992 | Oono et al. | 356/128 |
| 5,777,719 A | 7/1998 | Williams et al. | 351/212 |
| 6,082,856 A | 7/2000 | Dunn et al. | 351/160 H |
| 6,155,684 A | 12/2000 | Bille et al. | 351/212 |
| 6,312,373 B1 | 11/2001 | Ichihara | 515/359 |
| 2002/0085172 A1 | 7/2002 | Altmann | 351/178 |

FOREIGN PATENT DOCUMENTS

WO  03/068057  8/2003  ........... A61B/3/00

OTHER PUBLICATIONS

Thibos, L.N. et al., Standards for Reporting the Optical Aberrations of Eyes Optical Society of America 1999.

* cited by examiner

Primary Examiner—George Manuel
(74) Attorney, Agent, or Firm—Craig E. Larson

(57) ABSTRACT

A calibration component for use in calibrating and certifying the accuracy of an ophthalmic wavefront sensor comprises a monolithic, plano-convex refractive optic having known amounts of one or more selected aberrations induced by the spherical, axisymmetric aspherical, or non-axisyrmmetric aspherical convex surface. An alignment tool is described, along with a procedure for calibrating an aberrometer.

46 Claims, 9 Drawing Sheets

METHOD AND APPARATUS FOR CALIBRATING AND CERTIFYING ACCURACY OF A WAVEFRONT SENSING DEVICE

BACKGROUND OF THE INVENTION

1. Field of the Invention

The present invention pertains to the field of ophthalmic wavefront sensing and, particularly, to an apparatus and method for aberrometer calibration and accuracy certification.

2. Description of Related Art

A wavefront sensor, often referred to as an aberrometer (which term will be used interchangeably herein), is a device that measures a difference in the optical path of light between a deformed wavefront and an ideal, or reference, wavefront. The measurement, when properly processed, yields values for various aberrations in the optical system that the light propagates through and which deform the wavefront. Although high-energy lasers and astronomical imaging were primary drivers for wavefront sensor development (where the atmosphere itself was the aberration causing optical system), more recent attention has focused on measuring the aberrations of the eye with the goal of improving visual quality. The interested reader is directed to Geary, J M, *Introduction to Wavefront Sensors,* SPIE Optical Engineering Press (1995); Williams' U.S. Pat. No. 5,777,719, for more information. These references, to the extent permitted by applicable patent rules and laws, are herein incorporated by reference in their entirety.

The aforementioned Williams' patent describes a Shack-Hartmann type wavefront sensing instrument that can be used to measure, among other parameters, higher-order ocular aberrations. Many commercial aberrometers incorporate a microlens (lenslet) array and operate on the Shack-Hartmann principle. Other types of aberrometers include the spatially resolved refractometer based on the Scheiner optometer, those based on the Tscherning principle, Skiascopic systems, scanning systems of the Tracey technology type, raytracing devices, and others. All of these aberrometer types are well known in the ophthalmic wavefront sensing art so that a detailed description of these devices is not necessary to understand the invention. Descriptions of these devices can be found, for example, in *J. Refractive Surg.* 16 (5), September/October 2000.

Ocular wavefront data is increasingly being used to configure ablation algorithms for refractive surgery such as, e.g., PRK, LASIK, and LASEK, and for custom shaping of contact lenses, IOLs, onlays and other vision correcting elements. Successful outcomes to these applications depend upon the validity of the obtained aberration measurement which in turn depends on the correct initial calibration of the aberrometer, and on the correct calibration of the aberrometer when it is used to obtain diagnostic/therapeutic wavefront aberration measurements.

Basically, aberrometers have been calibrated for defocus only using spherical lenses. An Optical Society of America task force set up in 1999 made recommendations for a standard aberrator for calibration of aberrometers. The interested reader is directed to a paper by Thibos, L. N. et al., *Standards for Reporting the Optical Aberrations of Eyes* (Optical Society of America 1999). Initially, an aberrated model eye was contemplated but was abandoned as too elaborate in view of the different requirements of subjective and objective aberrometers. Instead, a pair of lenses of known spherical power was used as an aberrator, but there were problems with position sensitivity and control. An alternate aberrator design was a trefoil ($3^{rd}$ order aberration) phase plate. Phase plate aberrators, however, are disadvantageous for several reasons, namely: high sensitivity to misalignment due to tilt and decenter, external illumination preferably with a collimated beam, coherence effects such as speckle due to spatial coherence of collimated beam, limit on aberration quantity, high cost in material and time, and others.

Accordingly, the inventors have recognized a need for a method and apparatus that addresses these concerns and others relating to the calibration and accuracy of wavefront measurement and aberrometer operation.

SUMMARY OF THE INVENTION

An embodiment of the invention is directed to an improved aberrator or calibration component for an aberrometer. The calibration component preferably comprises a model eye and optionally includes a holder and an alignment tool. The model eye consists of a monolithic, convex anterior surface, refractive cylinder of transparent material for a desired wavelength. The convex, anterior surface can be a sphere, an axisymmetric asphere, or a non-axisymmetric asphere depending upon what aberrations are to be simulated. Alternatively, the anterior surface may be a perfect imaging conic and the posterior surface would have the complex shape that generates the aberrations. Both the anterior and the posterior surfaces can be formed by common fabrication techniques including diamond turning, grinding and polishing, laser machining, etching, molding, and so on. The material of the model eye can include optical glasses, plastics, crystals, and poly-crystalline materials. The model eye according to the invention is advantageous in that arbitrary wavefront aberrations including higher-order aberrations that are both axisymmetric and non-axisymmetric can be simulated accurately, surface alignment is accomplished during manufacture thus eliminating additional alignment, calibration of the model eye can be performed by interferometry and profilometry, the need for external sources or optics is eliminated, and they can be produced inexpensively and in volume through a molding process.

An aspect of the embodiment includes a holder for the model eye. The holder is preferably a self-aligning V-groove mount; however, other types of holders will be apparent to a person skilled in the art. In an associated aspect, an alignment tool is interchangeable with the model eye in the holder.

In another embodiment according to the invention, a method for calibrating an aberrometer for measuring ophthalmic wavefront aberrations includes the steps of providing a model eye having a known wavefront aberration; positioning the model eye along an optical axis of an aberrometer to be calibrated at a location that simulates a wavefront measurement of a patient's eye; aligning the model eye; and obtaining a wavefront measurement of the model eye. In an aspect of this embodiment, the known wavefront aberration is a defocus error for making a focus calibration of the aberrometer. In another aspect, the model eye has a toroidal convex surface for making a defocus and astigmatism calibration of the aberrometer. In another aspect, the model eye has a non-axisymmetric, convex surface for making a higher-order aberration calibration of the aberrometer. In another aspect, the model eye has a perfect imaging conic-shaped anterior surface and an aberration producing posterior surface.

These and other objects of the present invention will become more readily apparent from the detailed description to follow. However, it should be understood that the detailed description and specific examples, while indicating the preferred embodiments of the invention, are given by way of illustration only, since various changes and modifications within the spirit and scope of the invention will become apparent to those skilled in the art based upon the description and drawings herein and the appended claims.

BRIEF DESCRIPTION OF THE DRAWINGS

FIGS. 8–15 are graphical measurement representations of individual Zernike coefficients of the exemplary model eyes in Table I by two different aberrometers, and calculated values of the aberration coefficients.

DETAILED DESCRIPTION OF PREFERRED EMBODIMENTS

Figure 1:
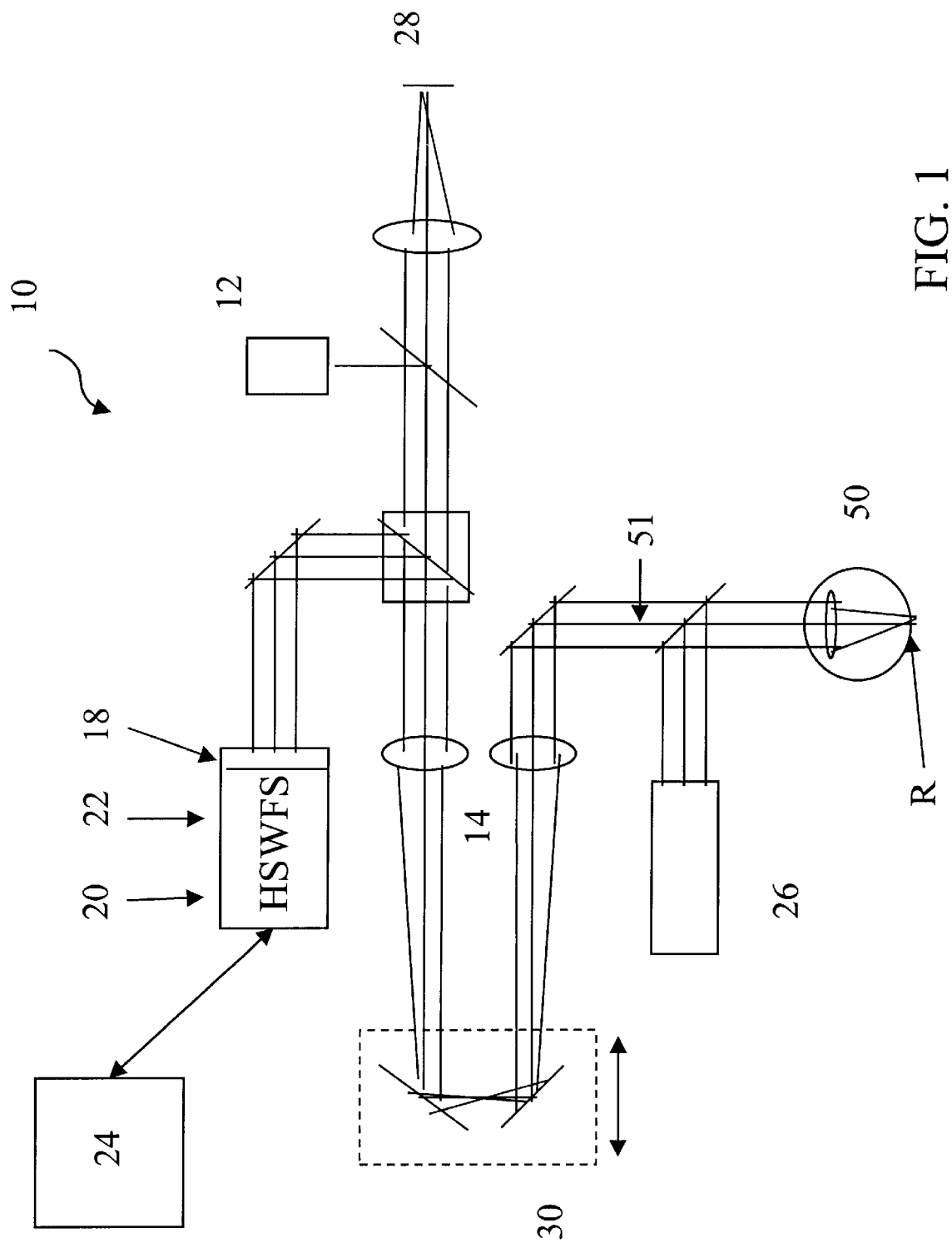
FIG. 1 is an optical schematic diagram of a generic Shack-Hartmann aberrometer.

FIG. 1 shows an optical diagram of a Shack-Hartmann aberrometer 10. It will be appreciated that the invention is not limited to use with a Shack-Hartmann aberrometer, but applies to any known aberrometer types and wavefront sensing methods for ophthalmic wavefront sensing. In general terms describing wavefront sensor operation, a patient's eye 50 is properly aligned with the measurement axis 51 of the aberrometer with the help of a fixation target 28 and an alignment camera 26, typically a pupil camera. The retina, R, of the eye is illuminated by light from a source 12 such as a 780 nm laser diode, for example, or other appropriate wavelength, semi-coherent source, and the light is focused on the retina by an optical trombone system 30 and imaging lenses 14. The trombone system (or an alternate optical focusing system known in the art) is used to compensate for the simple near- or far-sightedness in the eye and also sharpens the focus of the image spots formed on a detector 22, resulting in more accurate wavefront measurement. The interested reader is referred to International Publication WO 01/28408 for a detailed description of the optical trombone system. This publication is incorporated herein by reference in its entirety to the extent permitted by applicable patent rules and laws. Reflected light from the retina passes out through the eye's optical system and on to the detector 22. In the Shack-Hartmann system, which currently is the dominant ophthalmic device methodology for diagnostic wavefront measurement, the reflected light is focused by a lenslet array 18 into aerial images on the detector 22 and displayed by a sensor camera 20. Image centroids are calculated and wavefront slope data is obtained from image displacement information using a processing system 24 which includes a P.C. and appropriate software for also calculating the aberration data, for command and control of aberrometer components, for data transfer, and for other various calculations using the wavefront information. The information is processed and typically fit to Zernike polynomials to output the aberration coefficient measurements. These coefficients can then be used in the design of corrective lenses, ablation algorithms, and in other ophthalmic applications known to those skilled in the art.

Figure 2:
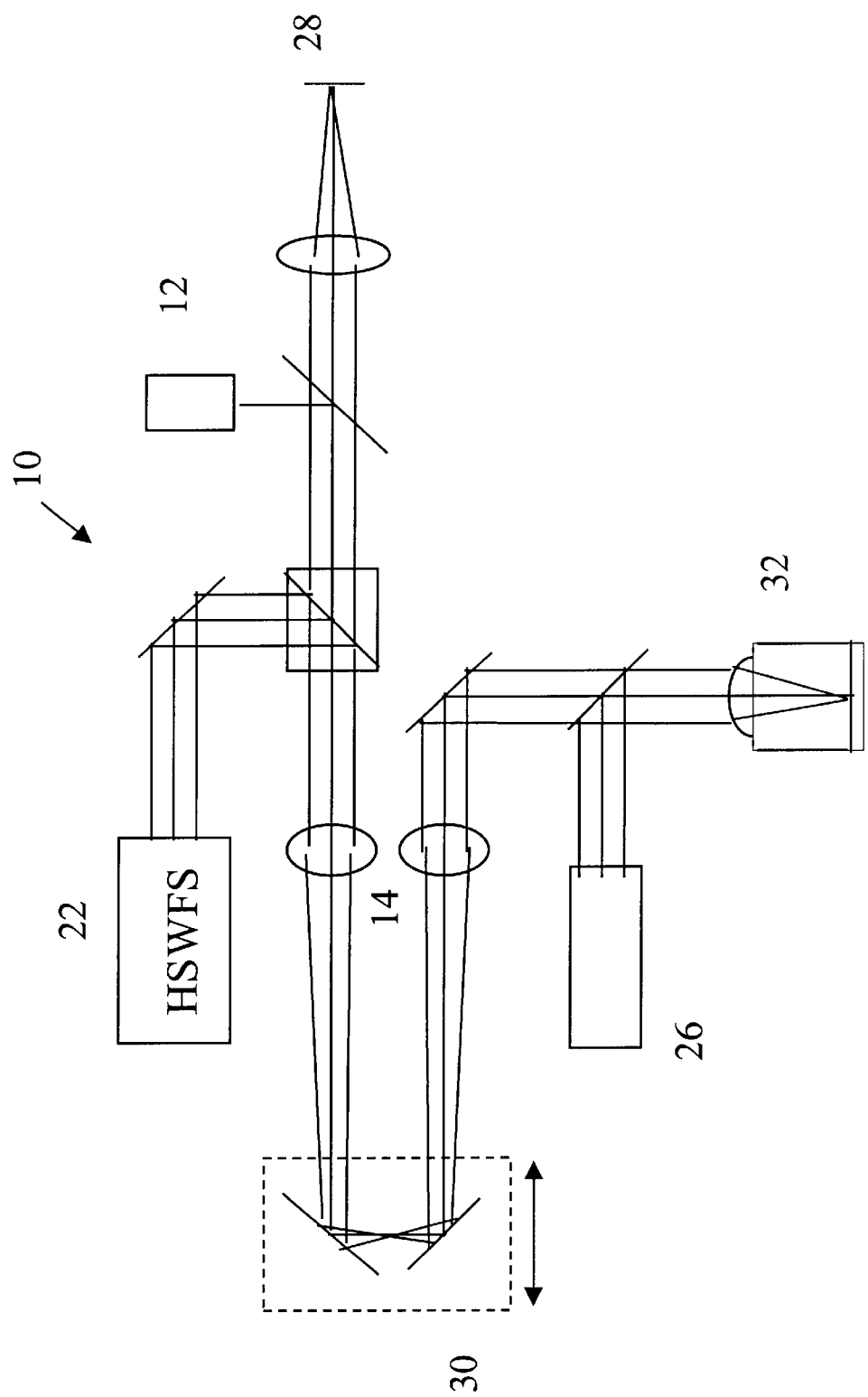
FIG. 2 is an optical schematic diagram of a Shack-Hartmann aberrometer incorporating a model eye according to an embodiment of the invention.
Figure 6:
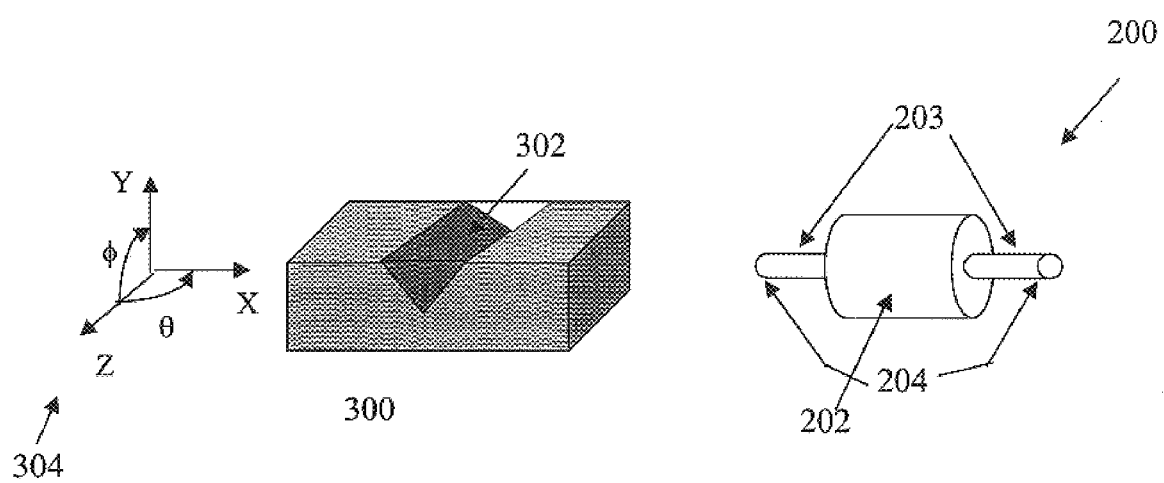
FIG. 6 is a schematic representation of a model eye holder according to an embodiment of the invention.
Figure 7:
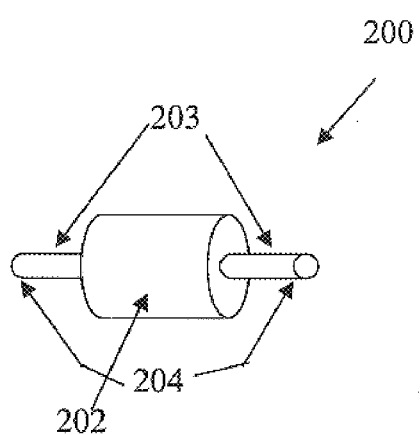
FIG. 7 is a schematic line drawing of an alignment tool according to an embodiment of the invention.

According to an embodiment of the invention described with reference to FIG. 2, a method for calibrating an aberrometer 10 for measuring ophthalmic wavefront aberrations requires providing a model eye 32 (discussed in more detail below) having a known wavefront aberration in a position to be occupied by the patient's eye (or in a conjugate pupil plane) thus simulating a wavefront measurement of the patient's eye; aligning the model eye 32 as the patient's eye would be aligned; and obtaining a wavefront measurement of the model eye. The alignment process is preferably accomplished with the aid of an alignment tool 200 shown in FIG. 7, although other alignment apparatus and methods will be apparent to those skilled in the art. The alignment tool 200 is a Plexiglas® cylinder having a center portion 202 with an outside diameter matched to that of the model eye, and two thinner end portions 203 each having a polished, plano surface 204.The end portions 203 are each about 1.5 mm in diameter thus providing a small entrance pupil which facilitates accurate tip/tilt alignment. A preferable model eye holder 300 as shown in FIG. 6 is a plate with a V-groove 302 that provides self-alignment for a cylindrical component such as the alignment tool and the model eye. It is cooperatively attached to a five-axis adjustment mount (not shown) allowing linear alignment adjustment in the x, y, and z planes and rotational adjustment about the z and y axes as shown by the coordinate system 304 in FIG. 6. The aberrometer 10 of FIG. 1 is equipped with a chin rest (not shown) to support the patient's head. In the alignment procedure, the chin rest is replaced with the model eye holder 300 and associated five-axis adjustment mount. The alignment procedure consisted of iteratively focusing the source light, via the trombone system, on the anteriorly positioned plano surface of the alignment tool and adjusting x,y position of the mount, and then focusing the source beam through the alignment tool onto the posteriorly positioned plano surface and adjusting x,y position, until the x,y positions for both focus points is the same. Azimuthal adjustments can be made as necessary. The model eye to be measured is then placed in the optical holder and the x, y, and z linear alignment is conducted using the pupil camera. The lens edges can be seen on the computer screen and centered by aligning the edges to on-screen horizontal and vertical reference lines. The z axis is then aligned so that the anterior surface of the model eye is in focus.

Figure 4:
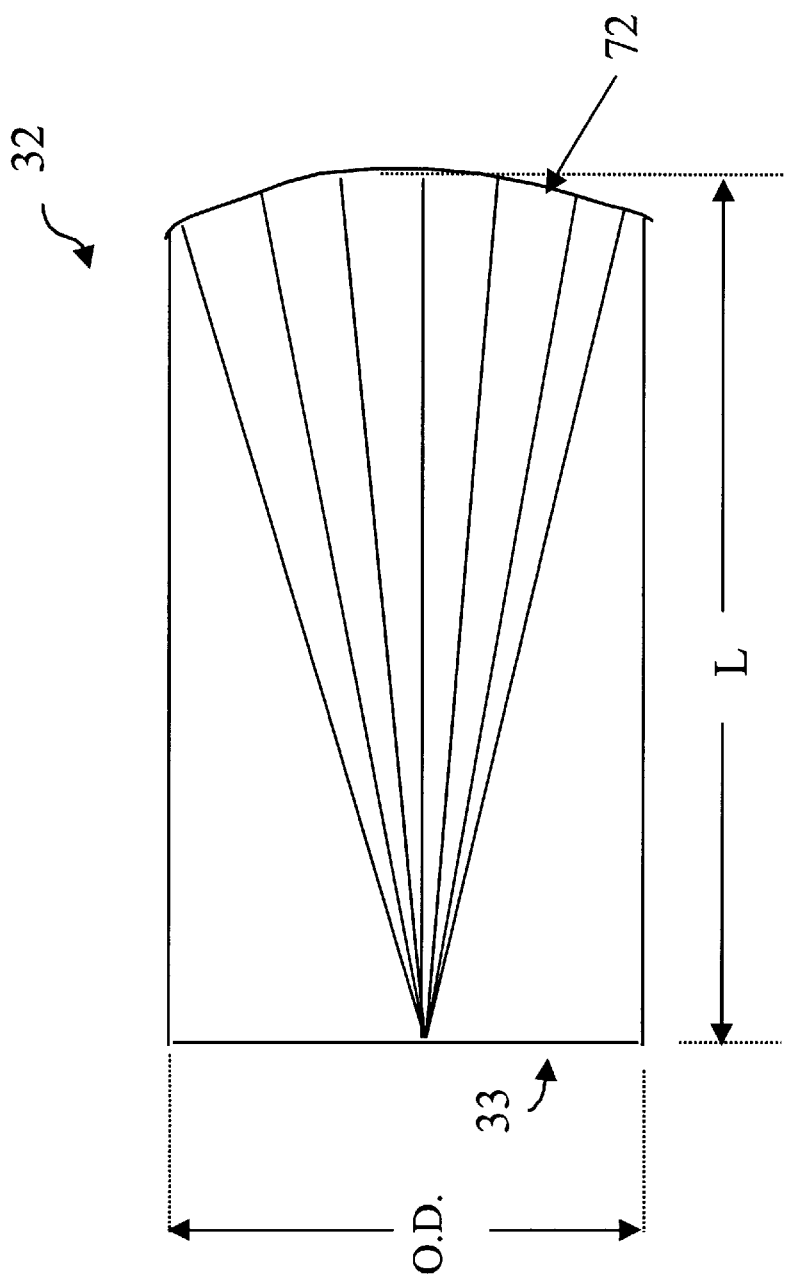
FIG. 4 is a cross sectional line drawing of a model eye according to the invention.

With reference to FIG. 4, a calibration component according to an embodiment of the invention, hereinafter referred to as a model eye 32, is a monolithic, plano-convex, refractive optic having a known amount of a desired aberration. The anterior, convex surface 72 can be a sphere, an axisymmetric asphere, or a non-axisymmetric asphere depending on what aberrations are to be simulated. For example, a spherical convex surface will produce defocus aberration and spherical aberration, and the two aberrations will be correlated. A convex, conic surface also will produce defocus and spherical aberration, but the two aberrations can be varied independently. A toric, convex surface (non-axisymmetric asphere) will produce defocus aberration, spherical aberration and astigmatism. Other non-axisymmetric aspheres will produce higher-order aberrations (known to those skilled in the art as corresponding to third- and higher-order Zernike coefficients or their equivalents). The model eye can also be bi-convex or meniscus as long as the anterior surface is a convex surface. In a preferred embodiment, the convex surface 72 is made by diamond turning on a 3-axis lathe such as an Optiform 50 lathe with a Variform oscillating tool post attachment (Precitech Corp., Keene, N.H.). Alternatively, both the piano 33 and convex 72 surfaces can be formed by common fabrication techniques including grinding and polishing, diamond-turning, laser machining, etching, molding, etc. The piano surface 33 can be roughened and coated with a corrective whitening liquid or otherwise made to diffusely reflect the source light akin to a real eye. The model eye preferably has an outside diameter (O.D.) sufficient to make the convex surface comparable to that of a real eye. The length, L, of the model eye preferably is in the range of the length of a real eye, typically between about 22 mm to 26 mm. The material of the model eye can be an optical glass (e.g., BK-7), a plastic (e.g., PMMA), a crystal, and a poly-crystalline material (e.g., ZnS), and in a preferred embodiment is polymethyl methacrylate (PMMA), which is diamond turnable, birefringent, transparent, and inexpensive. The birefringent property of PMMA is advantageous in that it reduces the spatial coherence of the laser light passing through the model eye, reducing the speckle and partial coherence effects during lenslet imaging.

Figure 5:
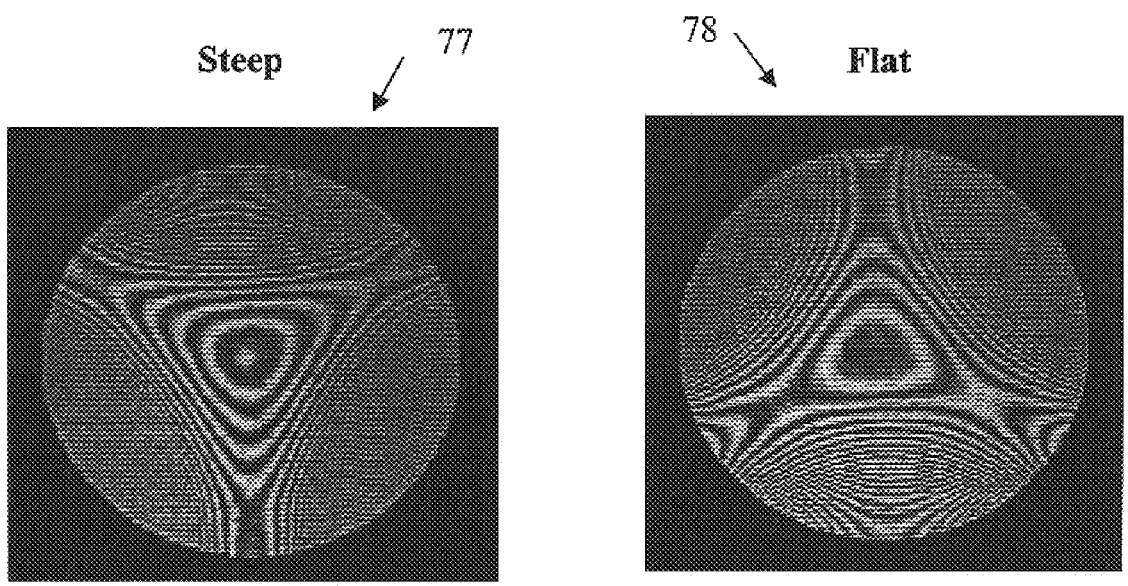
FIG. 5 is a reproduction of an optical interferogram of the anterior surface of an exemplary model eye according to the invention.
Figures 8, 9:
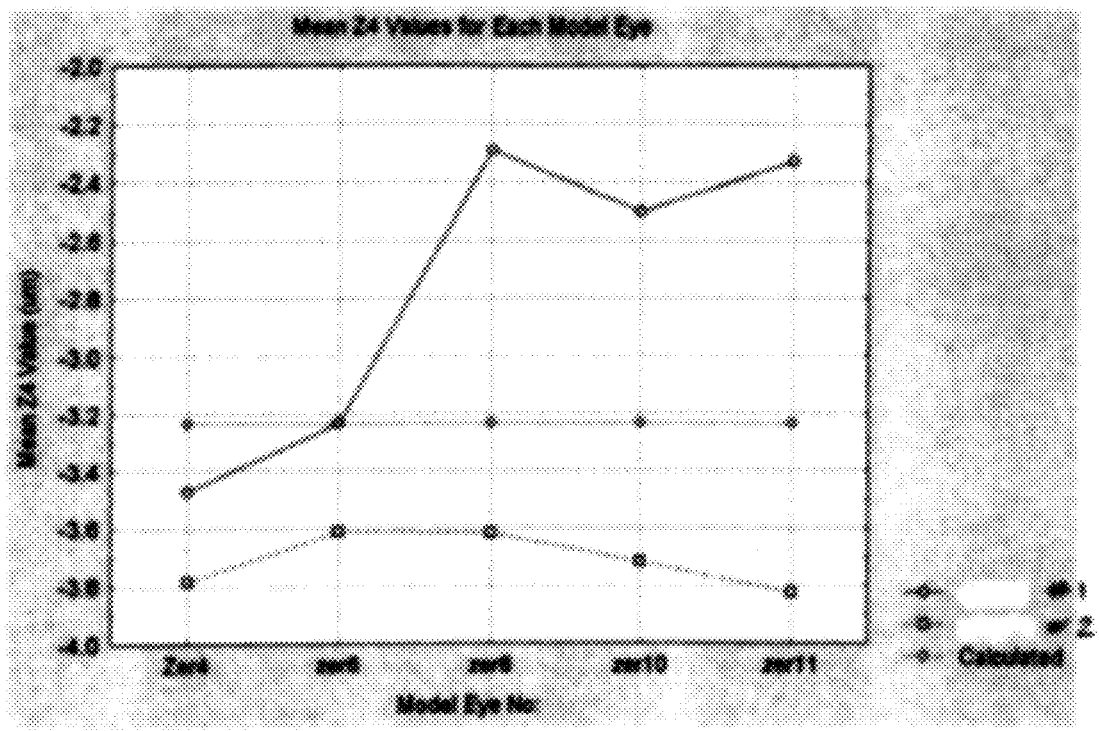
Figure 10:
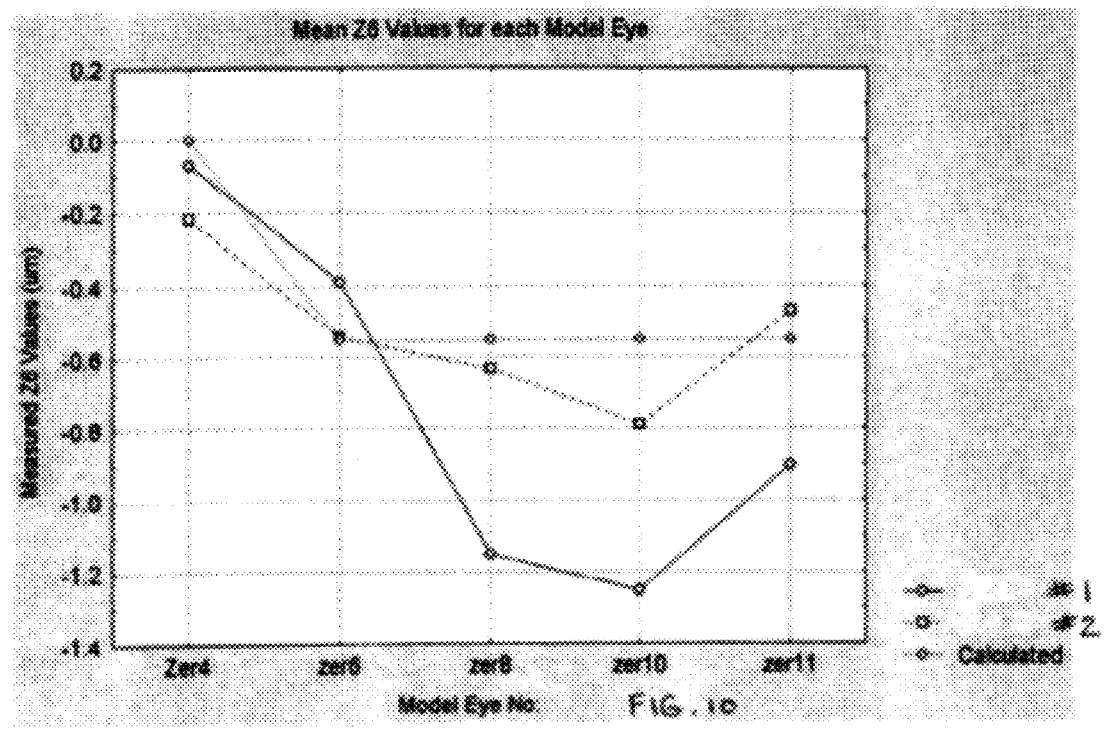
Figure 11:
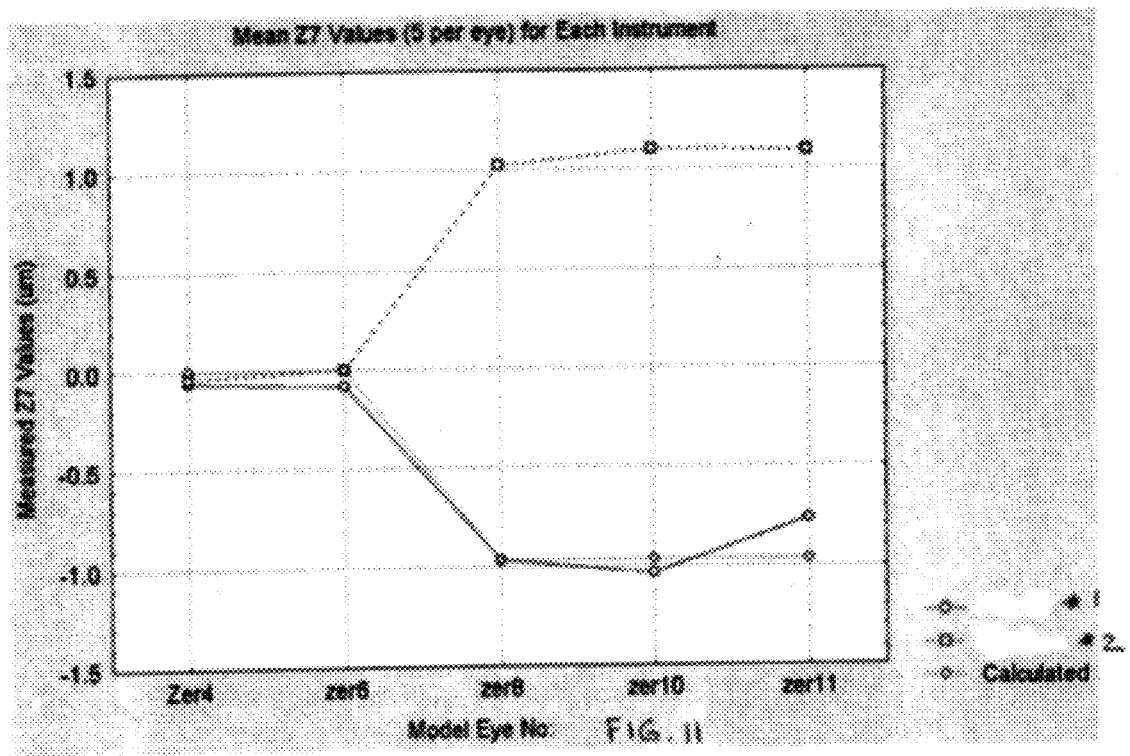
Figure 13:
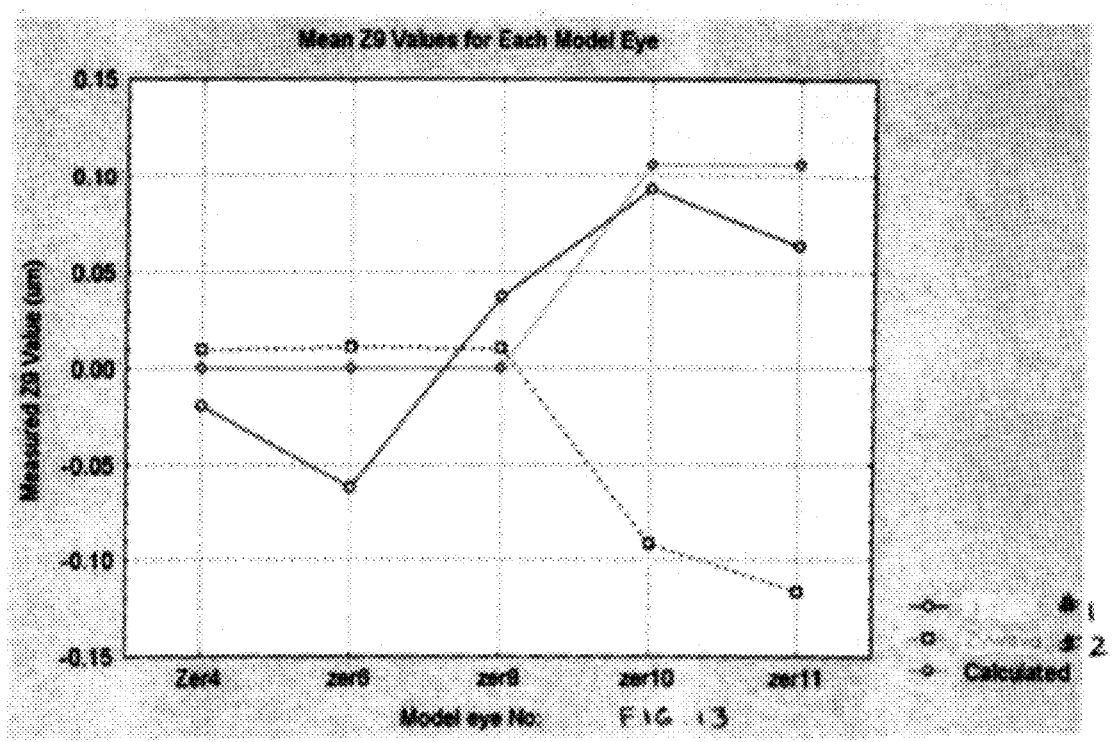
Figure 12:
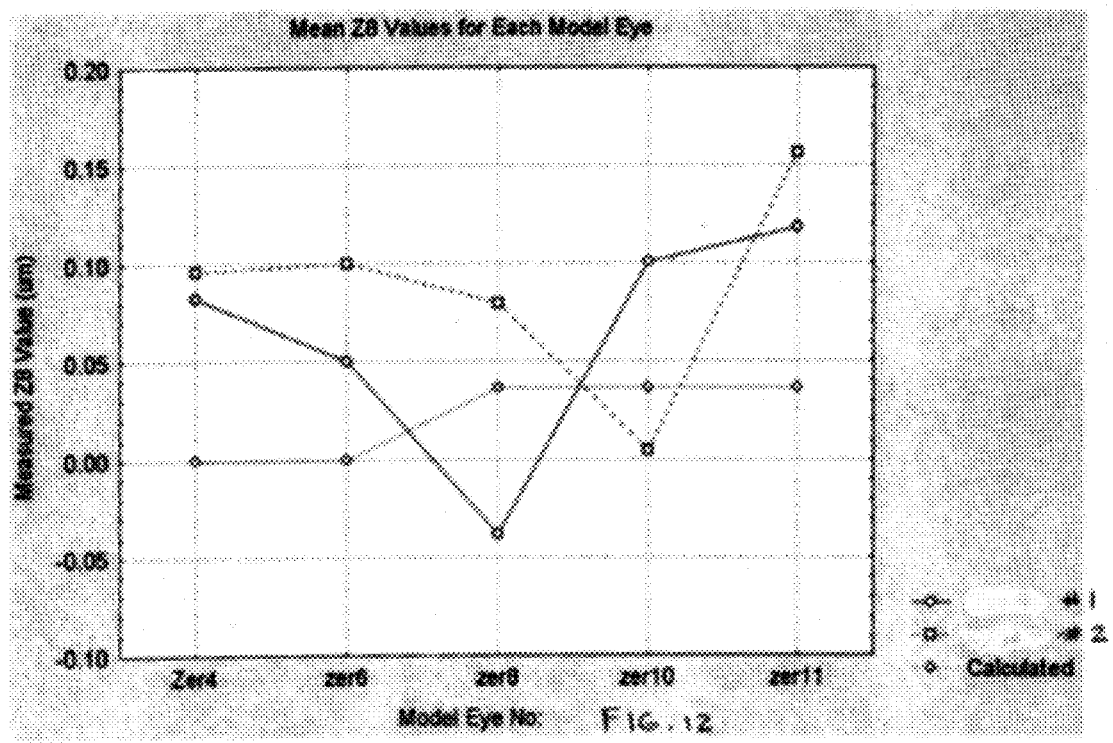
Figure 13:
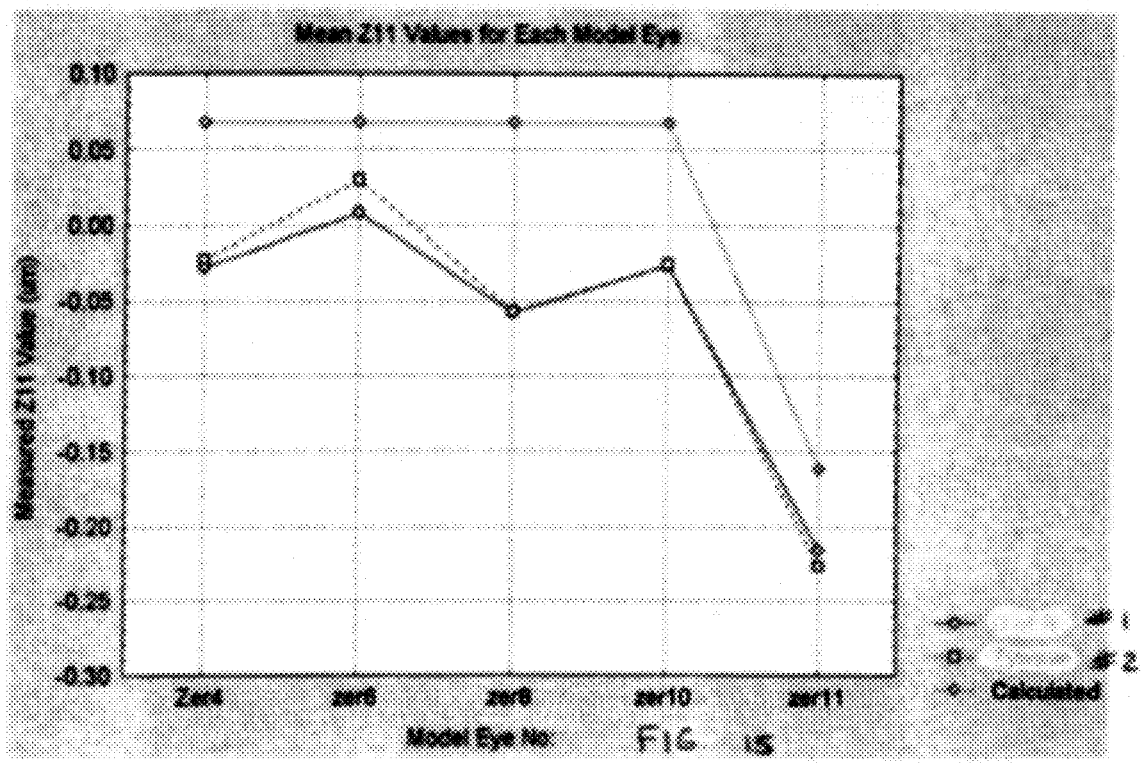
Figure 14:
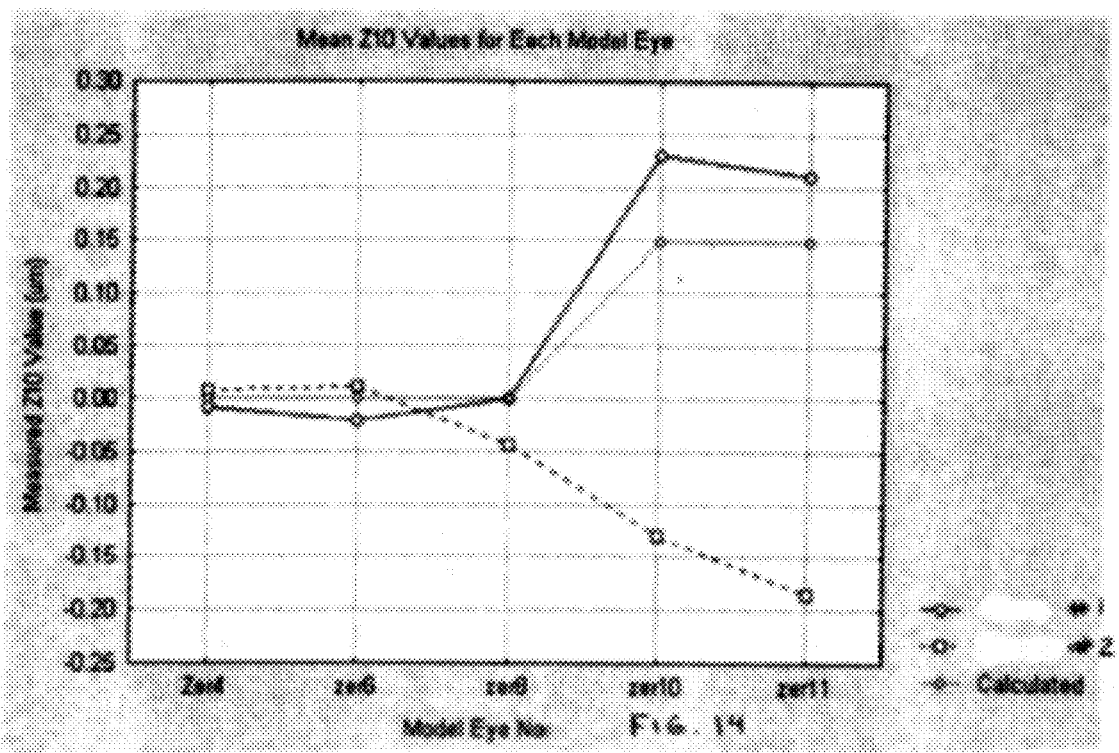

In an exemplary embodiment, the model eye 32 is a diamond-turned plano-convex cylinder of PMMA. The axial length, L, is 23.647 mm with an outer diameter of 12.7 mm. The prescription of the convex surface is as follows:

Vertex Radius, R=7.8 mm;

Conic Constant, k=0;

Coefficient for the 11th Zernike Term, Z330= 0.008652619 mm;

Normalization Radius, NR=4 mm;

Equation for the Sag of the Surface:

$$Z=(x^2/R)/[1+\sqrt{1-(1+k)*(x/R)^2}]+Z330*(x/NR)^3*\cos(3q)$$

where x is the radial coordinate in millimeters and q is the azimuthal coordinate in degrees or radians. The model eye 32 exhibits 1.89 micron of trefoil over an aperture of 5.7 mm at 780 nm. Interferograms 77,78 of the anterior surface 72 of the model eye 32 are shown in FIG. 5.

Additionally, a series of model eyes were diamond-point turned from Plexiglas using a 3-axis lathe. The optical surfaces of these simple optical systems were modeled using a single non-rotationally symmetric optic zone calculated to match the wavefront aberration of a patient with mild keratoconus who had been measured from an associated clinic population. The wavefront aberration was modeled using Zernike polynomials in a commercially available ray-tracing program called Zemax (Focus Software, Tucson, Ariz.). A series of model eyes were made which gradually incorporated additional Zernike components as shown in Table I.

TABLE I

| Model Eye Name | Zernike Co-efficients | Aberration Represented |
| --- | --- | --- |
| Z4 | $2^{nd}$ Order | Defocus |
| Z4-6 | $2^{nd}$ Order | Defocus & Astigmatism |

TABLE I-continued

| Model Eye Name | Zernike Co-efficients | Aberration Represented |
| --- | --- | --- |
| Z4-8 | $2^{nd}$ & $3^{rd}$ Order | Defocus, Astigmatism & Coma |
| Z4-10 | $2^{nd}$ & $3^{rd}$ Order | Defocus, Astigmatism, Coma & Triangular Astigmatism |
| Z4-11 | $2^{nd}$, $3^{rd}$ and $4^{th}$ Order | Defocus, Astigmatism, Coma, Triangular Astigmatism & Spherical Aberration |
| Z4-6 & Z11 | $2^{nd}$ & $4^{th}$ Order | Defocus, Astigmatism & Spherical Aberration |

The model eyes with defocus, astigmatism, and spherical aberration were verified using a ZYGO Mark-GPI interferometer. FIGS. 8–15 show measurements, by two different aberrometers, of individual Zernike coefficients Z4–Z11 of the exemplary model eyes in Table I and calculated values of the aberration coefficients.

Figure 3A:
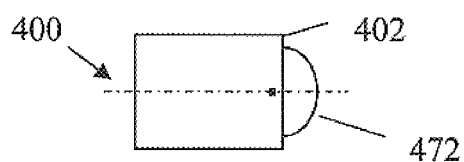
FIGS. 3a, b are side and front line drawing views, respectively, of a model eye aspect according to an embodiment of the invention.
Figure 3B:
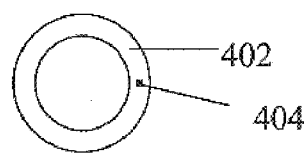

FIGS. 3a, b show an alternative model eye design according to the invention. In this aspect, model eye 400 has a flat, annular peripheral portion 402 encircling the convex surface 472. The peripheral portion 402 incorporates an orientation fiducial mark 404 for rotational positioning and alignment of the model eye. The mark 404, which can be a laser scribe, cut, imprinted indicia, or other suitable marking on a lens surface, allows repeatedly accurate positioning of model eyes having rotationally non-symmetric surfaces. It will be appreciated that the model eye need not have a flat periphery for locating the mark; rather, a fiduciary mark can also be located in a peripheral region of the actual convex surface of a model eye.

The measurement procedure for the model eye using the aberrometer is similar to that for a human eye. With reference to FIG. 2, the model eye 32 is placed at the same location as a patient's eye with the convex surface 72 receiving input illumination from the laser source 12. The narrow beam of infra-red laser energy passes through the center of the convex surface without much deviation because the beam diameter is small. The laser energy is brought to a focus at the plano surface 33 via the trombone system 30, and diffuisely reflects back toward the convex surface 72. The shape of the exiting wavefront depends upon the shape of the convex surface, the axial distance, L, between the convex and plano surfaces, and the index of refraction, n, of the model eye at the wavelength of interest. Thus, the shape of the wavefront can accurately be predicted by well-known ray-tracing techniques.

While various advantageous embodiments have been chosen to illustrate the invention, it will be understood by those skilled in the art that changes and modifications can be made therein without departing from the scope of the invention as defined in the appended claims.

I claim:

1. A calibration component for an aberrometer, comprising a monolithic, refractive optic having a convex anterior surface with a known amount of a desired aberration, wherein the desired aberration includes a higher-order aberration represented by a third-order or a higher-order Zernike polynomial or a mathematical equivalent thereof.

2. The component of claim 1, wherein the optic has substantially only the higher-order aberration corresponding to a single Zernike term.

3. The component of claim 1, wherein the optic has substantially only the higher-order aberration corresponding to a selected set of Zernike terms.

4. The component of claim 1, wherein the optic substantially excludes tilt, defocus and astigmatism corresponding to a first and second-order Zernike coefficient, respectively.

5. The component of claim 1, wherein the optic has a cylindrical shape with a length, L, and an outside diameter, O.D., wherein L>O.D.

6. The component of claim 1, wherein the calibration component is a model eye and wherein the anterior surface is a spherical surface.

7. The component of claim 1, wherein the calibration component is a model eye and wherein the anterior surface is an axisymmetric asphere.

8. The component of claim 1, wherein the calibration component is a model eye and wherein the anterior surface is a non-axisymmetric asphere.

9. The component of claim 1, wherein a posterior surface is plano and is a diffusely reflecting surface for a selected wavelength of light.

10. The component of claim 1, wherein the component is birefringent for a desired wavelength of light.

11. The component of claim 1, wherein the anterior surface is a diamond-turned surface.

12. The component of claim 1, wherein the anterior surface is at least one of a ground and polished, laser machined, etched, and a molded surface.

13. The component of claim 1, comprising an optical material that is transparent at a selected wavelength of light.

14. The component of claim 1, comprising at least one of an optical glass, a plastic, a crystal, and a poly-crystalline material.

15. The component of claim 1, wherein an anterior surface of the component has a planar peripheral portion and a convex remaining portion.

16. The component of claim 1, wherein the planar peripheral portion includes a fiducial orientation mark.

17. The component of claim 1, further comprising a holder for the optic.

18. The component of claim 17, wherein the holder has a self-centering V-groove.

19. The component of claim 17, further comprising a multi-axis adjuster cooperatively engaged with the holder.

20. The component of claim 17, further comprising an alignment tool having an end portion with a plano surface, another end portion, and an intermediate portion having a cross sectional dimension equal to a corresponding cross sectional dimension of the optic.

21. The component of claim 20, wherein the other end portion has a plano surface.

22. The calibration component of claim 1, having at least one of a plano-convex, a bi-convex, and a meniscus shape.

23. A model eye for use in calibrating an aberrometer for ophthalmic wavefront measurement, comprising a monolithic, refractive optic having a posterior surface and a convex anterior surface, said anterior surface having a known amount of an ocular aberration for a selected wavelength of light, and said posterior surface having a diffusely reflecting surface for said wavelength of light.

24. The model eye of claim 23 wherein said aberration corresponds to a second-order Zernike coefficient only.

25. The model eye of claim 23 wherein said aberration corresponds to a third-order Zernike coefficient only.

26. The model eye of claim 23 wherein said aberration corresponds to a combination of a second-order and a third-order Zernike coefficient only.

27. The model eye of claim 23 wherein said aberration corresponds to a combination of a second-order and a third-order and a fourth-order Zernike coefficient only.

28. The model eye of claim 23 wherein said aberration corresponds to a combination of a lower-order and a higher-order Zernike coefficient up to and including a fifth-order Zernike coefficient.

29. The model eye of claim 23 wherein said aberration corresponds to a higher-order Zernike coefficient only.

30. The model eye of claim 23 wherein said anterior surface is a symmetric, spherical surface.

31. The model eye of claim 23 wherein said anterior surface is an axisymmetric, aspherical surface.

32. The model eye of claim 23 wherein said anterior surface is a non-axisymmetric, aspherical surface.

33. The model eye of claim 23 wherein the optic has a cylindrical shape with a length, L, and a cross sectional dimension, O.D.

34. The model eye of claim 33, wherein the length, L, is between about 22 mm to 26 mm.

35. The model eye of claim 23, wherein the anterior surface includes a fiducial orientation mark.

36. The model eye of claim 23, wherein the anterior surface has a planar peripheral portion including a fiducial orientation mark.

37. A method for calibrating an aberrometer for measuring ophthalmic wavefront aberrations, comprising the steps of:
   providing a model eye having a known wavefront aberration;
   positioning said model eye along an optical axis of an aberrometer to be calibrated at a location that simulates a wavefront measurement of a patient's eye;
   aligning said model eye; and
   obtaining a wavefront measurement of the model eye.

38. The method of claim 37, wherein the known wavefront aberration is a defocus error for making a focus calibration of the aberrometer.

39. The method of claim 37, wherein the model eye has a toroidal, convex anterior surface for making a defocus and astigmatism calibration of the aberrometer.

40. The method of claim 37, wherein the model eye has a non-axisymmetric, convex anterior surface for making a higher-order aberration calibration of the aberrometer.

41. The method of claim 37, wherein the step of aligning said model eye comprises first positioning an alignment model eye capable of rotational alignment at the location that simulates a wavefront measurement of the patient's eye, aligning said alignment model eye, replacing the alignment model eye with the model eye, and further aligning said model eye.

42. The method of claim 37, wherein the step of aligning said model eye comprises using a pupil camera coupled to the aberrometer to align an x, y-axes positions of the model eye and focusing the posterior plano surface of the model eye to align a z-axis position of the model eye.

43. The method of claim 37, wherein the step of obtaining a wavefront measurement of the model eye comprises using a same illumination source for a calibration measurement as for a wavefront measurement of the patient's eye.

44. A method for making a focus calibration of an aberrometer used for measuring ophthalmic wavefront aberrations, comprising the steps of:
   providing a model eye having a known defocus error;
   positioning said model eye along an optical axis of an aberrometer to be calibrated at a location that simulates a wavefront measurement of a patient's eye; and
   obtaining a focus measurement of the aberrometer.

45. A method for making a defocus and astigmatism calibration of an aberrometer used for measuring ophthalmic wavefront aberrations, comprising the steps of:

providing a model eye having a well characterized toroidal convex anterior surface;

positioning said model eye along an optical axis of an aberrometer to be calibrated at a location that simulates a wavefront measurement of a patient's eye; and obtaining a defocus and astigmatism measurement of the model eye.

46. A method for making a higher-order aberration calibration of an aberrometer used for measuring ophthalmic wavefront aberrations, comprising the steps of:

providing a model eye having a well characterized non-axisymmetric, convex anterior surface, positioning said model eye along an optical axis of an aberrometer to be calibrated at a location that simulates a wavefront measurement of a patient's eye; and obtaining a higher-order aberration measurement of the model eye.

* * * * *